US008050480B2

(12) United States Patent
Noo et al.

(10) Patent No.: US 8,050,480 B2
(45) Date of Patent: Nov. 1, 2011

(54) METHOD AND IMAGE RECONSTRUCTION DEVICE FOR GENERATING COMPUTED TOMOGRAPHY IMAGE DATA

(75) Inventors: Frédéric Noo, Midvale, UT (US); Harald Schöndube, Erlangen (DE); Karl Stierstorfer, Erlangen (DE)

(73) Assignees: Siemens Aktiengesellschaft, Munich (DE); University of Utah Research Foundation, Salt Lake City, UT (US)

( * ) Notice: Subject to any disclaimer, the term of this patent is extended or adjusted under 35 U.S.C. 154(b) by 227 days.

(21) Appl. No.: 12/453,911

(22) Filed: May 27, 2009

(65) Prior Publication Data

US 2010/0046819 A1    Feb. 25, 2010

Related U.S. Application Data

(60) Provisional application No. 61/074,252, filed on Jun. 20, 2008.

(51) Int. Cl.
*G06K 9/00* (2006.01)
*A61B 6/00* (2006.01)

(52) U.S. Cl. .......................................... 382/131; 378/4

(58) Field of Classification Search ................. 382/128, 382/129, 130, 131, 132, 133, 134; 378/4, 378/21–27, 98.4, 98.6, 101, 901; 600/407, 600/410, 425, 427; 128/916, 920, 922
See application file for complete search history.

(56) References Cited

U.S. PATENT DOCUMENTS 4,458,267 A * 7/1984 Dolazza ........................ 378/98.7
7,170,975 B2 * 1/2007 Distler et al. ................. 378/150
7,372,937 B2 * 5/2008 Wang et al. ..................... 378/16
7,444,011 B2 * 10/2008 Pan et al. ....................... 382/131
7,477,720 B2 * 1/2009 Pack et al. ........................ 378/4

OTHER PUBLICATIONS

A. Katsevich, vol. 47, pp. 2583-2597 Analysis of an exact inversion algorithm for spiral cone-beam CT Phys. Med. Biol., 2002; Others.
Y. Zou et. al. Exact image reconstruction on PI-lines from minimum data in helical cone-beam CT Phys. Med. Biol., vol. 49, pp. 941-959, 2004; Others.
J. Pack et al., Cone-Beam Reconstruction Using the Backprojection of Locally Filtered Projections Med. Imag. vol. 24, No. 1, pp. 70-85, 2005; Others.
P. Danielsson et al. in Proc., pp. 141-144; Meeting on Fully 3D Image Reconstruction in Radiology and Nuclear Medicine (Pittsburgh, PA), D. Townsend et al. Eds., 1997; Others; US Towards Exact 3D-reconstruction for Helical Cone-Beam scanning of Long Objects. A New Detector Arrangement and a New Completeness Condition.

(Continued)

*Primary Examiner* — Abolfazl Tabatabai
(74) *Attorney, Agent, or Firm* — Harness, Dickey & Pierce, P.L.C.

(57) ABSTRACT

A method is disclosed for generating computed tomography image data of a volume of interest from X-ray CT data sets generated by a computed tomography system during scanning of an examination subject on a helical path rotating around a longitudinal system axis in the infeed direction. In at least one embodiment, at least two volume-based reconstructions of the volume of interest are performed by way of differential back-projection over surfaces constituted by different groups of M-lines, followed in each case by an inverse Hilbert transformation. The method further includes combining different reconstructed volumes to form a final reconstruction of the volume of interest.

17 Claims, 5 Drawing Sheets

OTHER PUBLICATIONS

C. Bontus et al. A quasiexact reconstruction algorithm for helical CT using a 3-Pi acquisiton Med. Phys., vol. 30, No. 9, pp. 2493-2502, 2003.

A. Katsevich, On two versions of a 3 algorithm for spiral CT Phys. Med. Biol., vol. 49, No. 11, pp. 2129-2143, 2004; Others.

C. Bontus et al. EnPiT: Filtered Back-Projection Algorithm for helical CT Using an n-Pi Acquisition IEEE Transaction Med. Imag. vol. 24, No. 8, pp. 977-986, 2005,; Others.

A. Katsevich Applied Mathematics Advances in Applied Mathematics, vol. 36, pp. 213-250, 2006; Others.

R. Proska et al. The n-PI-Method for Helical Cone-Beam CT IEEE Trans. Med. Imag., vol. 19, No. 9, pp. 848-863, 2000; Others.

D. Heuscher et al. Redundant data and exact helical cone-bema reconstruction Phys. med. Biol., vol. 49, pp. 2219-2238, 2004; Others.

T. Köhler et al. The Radon-Split Method for Helical Cone-Beam CT and its Application to Nongated Reconstruction IEEE Trans. Med. Imag., vol. 25, No. 7, pp. 882-897, 2006; Others.

A. Zanyatin et al. Helical CT Reconstruction with Large Cone Angle IEEE Nuclear Science Symposium Conference Record, vol. 4, pp. 2264-2267, 2006; Others.

A. Katsevich et al, . Beekman et al. Optimized reconstruction alogorithm for helical CT with fractional pitch between 1PI and 3PI Meeting on Fully 3D Image Reconstruction in Radiology and Nuclear Medicine, pp. 333-336, 2007; Others; DE.

Stierstorfer et al. Weighted FBP—a simple approximate 3D FBP algorithm for multislice spiral CT with good dose usage for arbitrary pitch Phys. Med. Bio. vol. 49, pp. 2209-2218, 2004; Others.

H. Kudo et al. Exact and approcimate algorithms for helical cone-beam CT Phys. Med. Biol. vol. 49, No. 13, pp. 2913-2931, 2004; Others.

G. Shechter et al. The fequency split method for helical cone-beam reconstruction Med. Phys., vol. 31, No. 8, pp. 2230-2236, 2004; Others.

X. Tang et al., Handling dara redundancy in helical cone beam reconstruction with a cone-angle-based window function and its asymptotic approximation Med. Phys., vol. 34, No. 6, pp. 1989-1998, 2007; Others.

H. Schöndube et al. F. Beekman et al. Towards an Efficient Two-Step Hilbert Algorithm for Helical Cone-Beam CT Meeting on Fully 3D Image Reconstruction in Radiology and Nuclear Medicine, pp. 120-123, 2007; Others; DE.

IEEE Nuclear Science Symposium Conference Record NSS '07, Comparative evaluation of two analytical methods for Helical Cone-Beam Tomography vol. 6, pp. 4467-4471, 2007; Others.

Towards Exact 3D-reconstruction for Helical Cone-Beam scanning ofLong Objects. A New Detector Arrangement and a New Completeness Condition Per-Erik Danielsson, Paul Edholm, Jan Eriksson, Maria Magnusson Seger; Others; US.

* cited by examiner

METHOD AND IMAGE RECONSTRUCTION DEVICE FOR GENERATING COMPUTED TOMOGRAPHY IMAGE DATA

PRIORITY STATEMENT

The present application hereby claims priority under 35 U.S.C. §119(e) on U.S. provisional patent application No. 61/074,252 filed Jun. 20, 2008, the entire contents of which is hereby incorporated herein by reference.

FIELD

At least one embodiment of the invention generally relates to a method for generating computed tomography image data of a volume of interest (VoI) from X-ray CT (computed tomography) data sets generated by a computed tomography system during scanning of an examination subject on a helical path rotating around a longitudinal system axis in an infeed direction (z-direction). At least one embodiment of the invention also generally relates to an image reconstruction device for generating computed tomography image data, for example using the method according to at least one embodiment of the invention.

BACKGROUND

A technique known as filtered back-projection (FBP) is nowadays used as the standard method for reconstructing computed tomography image data from a CT scanner's X-ray CT data sets for which, during data acquisition, an X-ray source from which conical or more specifically pyramidal X-ray beams are emitted rotates around a VoI on a helical path. With this method, the data is first pre-processed in order to make it as noise-free as possible. What is termed a "rebinning" step is then carried out in which the data generated with the beam fanning out from the source is rearranged such that it is present in a form as if the detector had been hit by an X-ray wave front approaching the detector in a parallel manner. The data is then transformed in the frequency domain. Filtering with what is termed a ramp filter takes place in the frequency domain and the filtered data is then inverse-transformed. Using the thus re-sorted and filtered data, back-projection onto the individual voxels within the volume of interest then takes place. Although this method works very well in principle, no mathematically exact reconstructions are possible, which may result in artifacts. In particular, because of their approximative mode of operation, the conventional FBP methods are subject to problems with low-frequency so-called cone-beam artifacts, particularly if the number of detector rows increases considerably and exceeds 100, as may be the case with the latest detectors.

A method has therefore been developed with which mathematically exact and stable reconstruction is possible even if there are incomplete projections among the incoming projection data. With this method, "differential back-projection" along so-called "π-lines" is performed. In this context, π-lines denote straight lines which intersect the helical path twice within one complete revolution. The back-projection data thereby obtained corresponds to the Hilbert transform of the desired image data, so that the desired image data can be generated by subsequent inverse Hilbert transformation. This method of three-dimensional differential back-projection followed by inverse Hilbert transformation (DBP-HT) is described in more detail in the publication by H. Schöndube, K. Stiersdorfer, F. Dennerlein, T. White and F. Noo: "Towards an efficient two-step hilbert algorithm for helical cone-beam CT," in Proc. 2007 Meeting on Fully 3D Image Reconstruction in Radiology and Nuclear Medicine (Lindau, Germany), F. Beckman and M. Kachelrieβ, Eds., 2007, pp. 120-123. As the method is theoretically mathematically exact and no artifacts due to the fan beam geometry of the X-ray beam can occur, it can be used to reconstruct good images even when the number of detector rows is markedly increased, as described above.

However, these reconstruction methods have so far been limited to using detector measurement data which is present on the detector within the so-called Tam-Danielsson window (also referred to hereinafter as the "TD window" for short), said TD window being defined by the projection of the X-ray source trajectory, i.e. the helical orbit of the X-ray source, onto the detector. Data that is measured in detector areas outside said TD window has hitherto been unusable in the DBP-HT method. However, since in normal CT systems the conical beam of the X-ray source is implemented such that it is incident on the entire detector, dose is consequently wasted. Although it would be theoretically possible to implement an X-ray source such that it produces an X-ray beam that is precisely incident on the TD window, this would mean no more flexibility in setting the pitch of the helical curve and would also be very cost-intensive, so that it makes more sense to use a rectangular standard detector and a conventional X-ray source. Apart from that, it would be very desirable to be able to use data outside the TD window. This data is redundant data which does not necessarily have to be used for a complete reconstruction. On the other hand, however, the redundant data is very useful for reducing image noise without affecting the resolution of the images. The redundant data could in principle be used with approximative methods, but again at the expense of the advantage of the mathematically exact reconstruction described above. Although an approach for exact mathematical reconstruction in which detector data outside the TD window could also be used is already described in the publication by J. Pack, F. Noo and R. Clackdoyle: "Cone-beam reconstruction using the backprojection of locally filtered projections" IEEE Trans. Med. Imag., vol. 24, no. 1, pp. 70-85, January 2005, this method is limited to performing differential back-projection and subsequent inverse Hilbert transformation for each individual voxel, multiple reconstructions and then averaging of the reconstruction values of the individual voxels being necessary in each case for the individual voxels. This results in a considerable computational complexity in order to reconstruct a complete volume of interest. This method is therefore very inefficient and hardly usable in day-to-day practice.

SUMMARY

In at least one embodiment of the present invention, an image reconstruction method is disclosed that is as efficient but also as mathematically exact as possible, and an image reconstruction device is disclosed, wherein the X-ray CT data sets can be measured in a conventional CT scanner with a rectangular, cylindrical detector and a cone-beam X-ray source rotating on a helical path.

In the method according to at least one embodiment of the invention, at least two volume-based reconstructions of the volume of interest are carried out by way of differential back-projection over surfaces formed by groups of M-lines, followed in each case by an inverse (finite) Hilbert transformation, an M-line being understood as meaning a line in the scanning chamber which connects an X-ray source position to any point on the detector. The term "M-line" is here an acronym for measurement line. It is clear from this definition of the M-lines that a plurality of M-lines runs through each voxel in the space and that, for example, each of the π-lines used hitherto for reconstruction is also an M-line, but not necessarily vice versa.

In at least one embodiment, for the reconstructions, groups of M-lines are inventively selected in each case from different of the following M-line subsets:

i) A first M-line subset which is selected such that a surface constituted by the respective M-lines of the M-line group meets the detector surface completely within the TD window. In other words, the M-line subset is defined such that, when a corresponding group or family of M-lines constituting the desired surface is selected, said surface does not then meet detector areas that are outside the TD window on the detector surface.

ii) A second M-line subset which is selected such that a surface constituted by the respective M-lines of the M-line group intersects a detector area before the TD window when viewed along the scanner axis in the infeed direction. Here a group of M-lines is therefore selected in each case such that the line of intersection of the surface constituted thereby with the detector does not currently lie completely in the TD window, but meets, at least in part, the detector area which lies before the TD window in the z-direction, i.e. in the helical trajectory infeed direction running along the z-axis or scanner axis.

iii) A third M-line subset which is selected such that a surface constituted by the respective M-lines of the M-line group intersects a detector area after the TD window when viewed along the scanner axis in the infeed direction. This is therefore the reverse case of the previously mentioned area in which the M-line group is selected such that the line of intersection between the surface constituted by the M-lines and the detector surface lies at least partly in an area after the TD window when viewed in the z-direction.

The different reconstructions are then combined to form a final reconstruction of the volume of interest, e.g. averaged in the simplest case.

In at least one embodiment of the method described, reconstruction is therefore not limited to the very restricted set of all the π-lines, but it is also possible to select from a larger number of M-lines, the M-lines being selected such that data outside the TD window can also be included. It has been found that, in the case of such volume-based reconstruction on surfaces constituted by M-lines, by suitably combining the volumes generated during the reconstructions the measurement data outside the TD window can be used to achieve a reduction in image noise overall. As the method is not geared to reconstructing individual voxels, but entire volumes can be reconstructed over surfaces, the computational complexity compared to the method, mentioned in the introduction, of reconstruction purely on π-lines is essentially only increased by a factor corresponding to the number of individual reconstructions to be combined, which is no longer an issue in the context of today's computing capabilities. It must be emphasized that the reconstruction method according to the invention is just as mathematically exact as reconstruction on π-lines, so that in spite of the inclusion of detector data outside the TD window, no additional artifacts caused by the conicity of the X-ray beam can be produced.

A corresponding image reconstruction device for generating computed tomography images of a volume of interest from X-ray CT data sets generated during scanning of the examination subject on a helical path rotating around a longitudinal scanner axis in an infeed direction requires, on the one hand, a raw data interface for transferring the X-ray CT data sets and, on the other, an X-ray CT data selection and calculation module which is designed to carry out the required number of reconstructions of the volume of interest by way of differential back-projection over surfaces formed by different groups of M-lines, followed in each case by inverse Hilbert transformation and, in doing so, to select the groups of M-lines for the reconstructions from the M-line subsets already described above. The image reconstruction device additionally requires a volume image data combining unit in order to combine the different reconstructions to produce a required final reconstruction, i.e. the desired computed tomography volume image data of the volume of interest, and finally an image data interface for outputting the computed tomography image data generated.

Such an image reconstruction device can be part of a computed tomography system, i.e. it can be installed in the usual manner, for example, on a control and evaluation computer of the tomography system. Basically, however, an image reconstruction device of this kind can also be implemented in other computer units which are e.g. connected to a computed tomography system via a network for data transfer or can be supplied with corresponding data in some other manner. The X-ray CT data selection and calculation module and the volume image data combining unit can be implemented as software modules on a suitable computer. The raw data interface and the image data interface can likewise be implemented in the form of pure software, provided only transfer of the X-ray CT data sets and/or outputting of the image data to/from other additional raw data preprocessing units and/or image data further processing units on the same computer unit is required. Basically, however, these interfaces can also be implemented as hardware/software interfaces in order to implement an external output, e.g. using hardware interfaces specially configured by software components. Output of the computed tomography image data is not to be understood as only meaning outputting to a screen, a printer or the like, but each output of computed tomography image data by the image reconstruction device, e.g. storing of the image data for subsequent inspection or further processing in a memory.

An advantage of a purely software implementation is that hitherto used image reconstruction devices can also be simply upgraded by a software update in order to operate in the inventive manner. In this respect at least one embodiment is also directed to a computer program product which can be directly loaded into a memory of a programmable image reconstruction device, having program sections for performing all the steps of the method according to at least one embodiment of the invention when the program is executed in the image reconstruction device.

Further advantageous embodiments and further developments of the invention will emerge from the dependent claims and the following description. The image reconstruction device according to at least one embodiment of the invention can also be further developed analogously to the dependent method claims.

Various methods can be used to combine the different reconstructions performed over the different surfaces. Simple averaging, possibly also weighted averaging, of the image data generated during the reconstructions can be performed in each case. For such averaging, a mean intensity value is obtained from the intensities of the mutually corresponding voxels in the different volume image data.

Although in principle any number of reconstructions can be used for carrying out at least one embodiment of the method, the complexity involved in the overall calculation of the image data increases with each additional reconstruction. For the simplest case, i.e. that only two reconstructions are performed on two different surface types, at least one of the reconstructions is preferably carried out using a group of M-lines from the first M-line subset and at least one other of the reconstructions is carried out using a group of M-lines from the second or third M-line subset. In other words, it is ensured that at least one reconstruction is performed over a plane that lies completely in the TD window in order to enhance the quality, and contains another reconstruction of redundant data.

In order to take into account all the data acquired by the detector as far as possible, i.e. outside the TD window the areas both before and after the TD window in the z-direction, preferably at least one reconstruction must be carried out using a group of M-lines from the first M-line subset and at least one other reconstruction using a group of M-lines from the second M-line subset and at least one third reconstruction using a group of M-lines from the third M-line subset. Weighing up the efficiency aspects versus the quality aspects, it is particularly preferred to carry out precisely three reconstructions, each reconstruction being performed with M-line surfaces from another M-line subset, i.e. a reconstruction over surfaces which completely intersect the detector in the TD window, a reconstruction over surfaces which intersect the detector before the TD window, and a reconstruction over surfaces which also intersect the detector in an area after the TD window. For this variant, although only three reconstructions need to be performed, all the data obtained by the detector is taken into account.

In order to be able to carry out the combining of the various reconstructed volume image data, particularly the averaging, with as little computational complexity as possible, the volume image data generated during the individual reconstructions is first transformed into Cartesian coordinates. In other words, all the volume image data of the reconstructions is, for example, first converted into the examination subject's coordinate system which is fixed with respect to the examination subject (patient coordinate system). This transformation into the Cartesian coordinates can also be performed by way of an interpolation. After the transformation, all the reconstructions are available in the same coordinate system so that, for example, the intensities of the individual voxels can be averaged quickly and simply.

Preferably, interpolated detector data is likewise used to perform the reconstruction, i.e. additional detector data is interpolated between the detector data actually measured. The advantage of this is that the M-lines to be selected are not limited by the individual detector fields, but the M-lines can be selected such that they are optimum for the reconstruction. In particular, the detector data can also be interpolated here between the detector data actually measured, such that the M-lines constituting the respective surface appear projected in parallel onto a plane perpendicular to the longitudinal axis of the computed tomography system used for acquiring the X-ray CT data sets. Particularly advantageously it is also ensured that the M-line projections in question are implemented in an equidistant manner. In addition, it can also be ensured that the M-lines constituting the respective surface are selected such that they all fall on the same detector row. This arrangement considerably facilitates the calculation for the reconstruction and thus ensures a higher reconstruction rate.

In order to fully utilize the detector area, it is preferably ensured as early as acquisition of the X-ray CT data sets, i.e. during scanning of the examination subject, that the helical X-ray source trajectory around the region of interest is selected such that the TD window on the detector surface is adjacent to the outer edges of the two outermost detector rows. This ensures that the TD window just fits the detector.

This can be predefined by the thread pitch of the helical trajectory, i.e. by adjusting the infeed rate between examination subject and X-ray source in the z-direction in relation to the rotational speed of the X-ray source in the x/y-plane.

For the subsequent reconstruction, it can then preferably be ensured that M-line surfaces which precisely meet the front or back edge, in the z-direction, of the detector are taken into account for the reconstruction in order to maximize the set of redundant data used in the reconstruction and achieve as low image noise as possible.

BRIEF DESCRIPTION OF THE DRAWINGS

The invention will now be explained again in greater detail by way of example embodiments and with reference to the accompanying drawings, in which.

DETAILED DESCRIPTION OF THE EXAMPLE EMBODIMENTS

Figure 1:
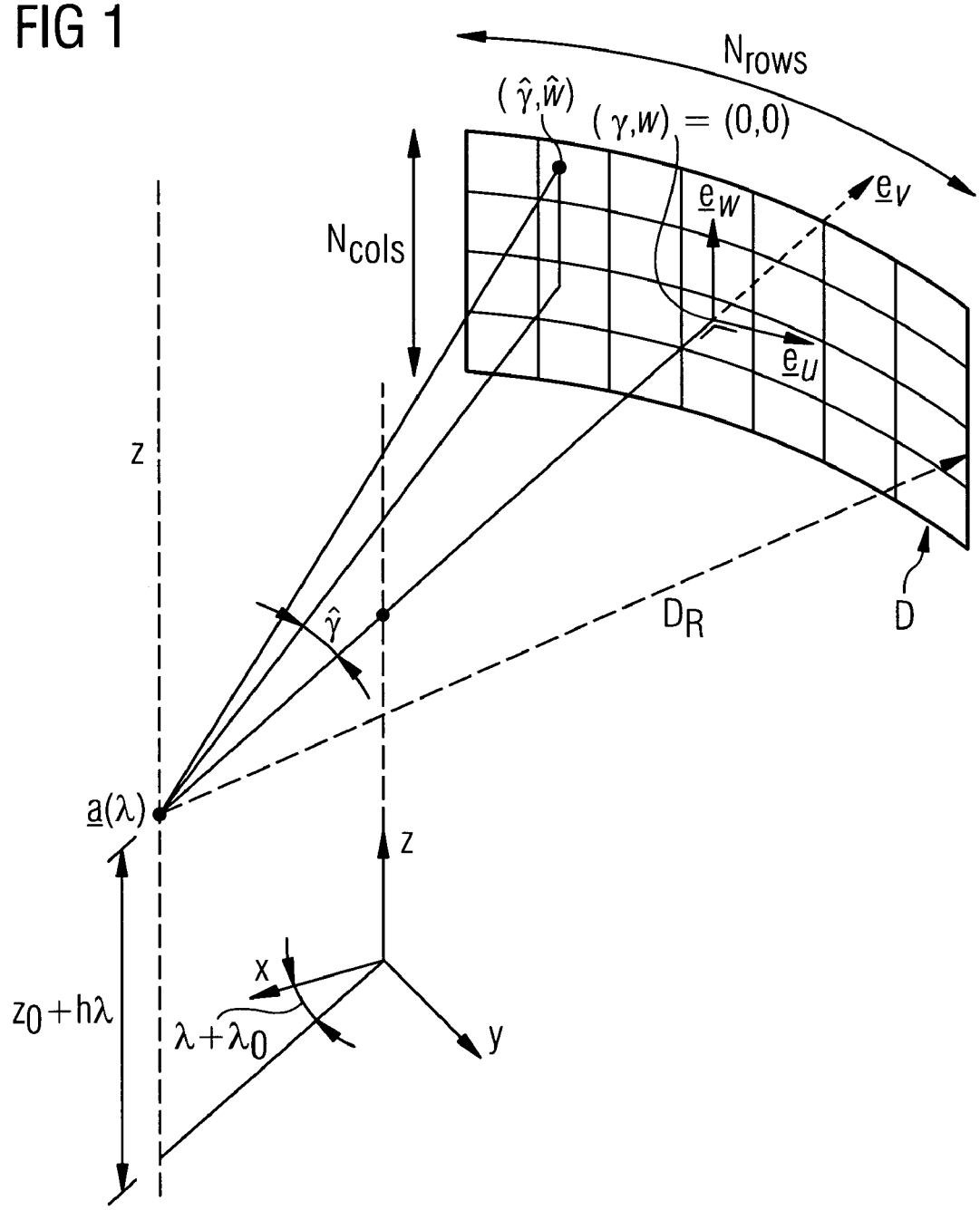
FIG. 1 schematically illustrates the data acquisition geometry in the CT system.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The data acquisition geometry and the designations used below will now be explained with reference to FIG. 1.

The three-dimensional density distribution to be reconstructed is denoted here as f(x), where x=(x, y, z) is a vector in the Cartesian coordinate system. It is assumed that the Cartesian coordinate system (x, y, z) is fixed with respect to the examination subject and the z-axis corresponds to the direction in which the examination subject is moved relative to the CT scanner during a revolution of the X-ray source, i.e. the z-axis is ultimately the system axis along which the helical trajectory moves in an infeed direction (in the direction of positive z-values).

In CT systems with an X-ray beam cone, the movement of the apex of the cone, i.e. the movement of the X-ray source relative to the examination subject, i.e. the patient, on the helical path is described as follows:

$$\underline{a}(\lambda)=[R_0 \cos(\lambda+\lambda_0), R_0 \sin(\lambda+\lambda_0), z_0+h\lambda] \quad (1)$$

where $R_0$ is the radius and $2\pi h$ specifies the pitch of the helical path. $\lambda$ is a free variable between a selected start point $\lambda_{start}$ and a selected end point $\lambda_{end}$ which describes the angular position of the apex and therefore of the X-ray source. $\lambda_0$ and $z_0$ specify the coordinates of the X-ray source at the instant $\lambda=0$.

In the following it will be assumed that a usual rectangular, cylinder-segment-shaped detector D used, as schematically illustrated in FIG. 1. Such a detector D has $N_{rows}$ detector rows with $N_{cols}$ detector elements which together form a cylinder segment with a radius $D_R$ around the apex. To mathematically describe the position on the detector, i.e. the position of the detector elements, relative to the examination subject, three orthogonal unit vectors can be used which rotate about the z-axis with the variable $\lambda$:

$$\underline{e}_u(\lambda)=[-\sin(\lambda+\lambda_0), \cos(\lambda+\lambda_0), 0] \quad (2)$$

$$\underline{e}_v(\lambda)=[-\cos(\lambda+\lambda_0), -\sin(\lambda+\lambda_0), 0] \quad (3)$$

$$\underline{e}_w=[0,0,1] \quad (4)$$

These are disposed such that $\underline{e}_v$ is parallel to the (x, y) plane and defines the direction of a line from the apex to the detector which intersects the z-axis. The point of intersection of this straight line with the detector simultaneously also defines the origin of the detector coordinates. The other directions of the detector coordinates are then defined by $\underline{e}_w$ which is parallel to the z-axis, and by $\underline{e}_u$, which is defined such that the three unit vectors $\underline{e}_u$, $\underline{e}_v$, $\underline{e}_w$ constitute the orthonormal base of a three-dimensional space $R^3$. Because of the detector geometry selected, projections of the detector rows onto the $\underline{e}_u/\underline{e}_w$ plane are parallel to $\underline{e}_u$. On the detector D itself, measurement values are acquired in equidistant detector coordinates w and $\gamma$. The coordinate w denotes the detector row and is counted in the direction of the dimension $\underline{e}_w$, while $\gamma$ defines the fan angle of the detector column, i.e. the angle between two planes, namely the plane which contains the apex and the z-axis, and the plane containing the apex and the respective detector column. Positive values of the coordinate $\gamma$ correspond to the positive directions of the unit vector $\underline{e}_u$ in the detector coordinate system.

For a geometry thus defined, data acquisition can be defined as follows:

$$g(\lambda, \gamma, w) = \int_0^\infty f(\underline{a}(\lambda) + t\underline{\alpha}(\lambda, \gamma, w))\, dt \quad (5)$$

where $\alpha(\lambda, g, w)$ describes a unit vector which points from $\underline{a}(\lambda)$ to a detector element at the fan angle $\gamma$ and in the detector row w, i.e.

$$\underline{\alpha}(\lambda, \gamma, w) = \frac{(D\sin\gamma\, \underline{e}_u(\lambda) + D\cos\gamma\, \underline{e}_v(\lambda) + w\underline{e}_w)}{\sqrt{D^2 + w^2}} \quad (6)$$

In this geometry, the top boundary $w_{top}$ and bottom boundary $w_{bottom}$ of the TD window (TD) can be described as follows:

$$w_{top} = \frac{Dh}{R_0}\frac{\pi/2 - \gamma}{\cos\gamma}, \quad w_{bottom} = \frac{Dh}{R_0}\frac{\pi/2 + \gamma}{\cos\gamma}. \quad (7)$$

At this juncture it should be noted that, with the geometries shown in the figures, the z-axis points perpendicularly upward in each case. In reality it is usually the case that the z-axis lies vertically. The terms "bottom" and "top" boundary for the TD window must therefore be understood in the sense that, in the z-direction, the lower limit is before the TD window and the upper limit is after the TD window. As already explained, the TD window is defined by the projection of the helical path onto the detector surface. The TD window is illustrated in the central part of FIG. 3 in which the TD window TD is marked as a hatched area inside the unhatched detector D.

Before back-projection of the CT data sets is performed, so-called rebinning into a pseudoparallel wedge geometry first takes place. This method is described more precisely, for example, in K. Stierstorfer, A. Rauscher, J. Boese, H. Bruder, S. Schaller and T. Flohr: "Weighted FBP—a simple approximate 3D FBP algorithm for multislice spiral CT with good dose usage for arbitrary pitch." Phys. Med. Biol., vol. 49, pp. 2209-2218, 2004 and D. Heuscher, K. Brown and F. Noo: "Redundant data and exact helical cone-beam reconstruction." Phys. Med. Biol., vol. 49, pp. 2219-2238, 2004, the entire contents of each of which are hereby incorporated herein by reference.

This rebinning can be described mathematically as follows using the rebinning equations:

$$g_r(\vartheta(\lambda, \gamma), s_r(\lambda, \gamma), w) = g(\lambda, \gamma, w), \quad (8)$$

$$\vartheta(\lambda, \gamma) = \lambda + \frac{\pi}{2} - \gamma, \quad s_r(\lambda, \gamma) = R_0 \sin\gamma \quad (9)$$

where the variable w remains unchanged. With rebinning of this kind, which ultimately corresponds to a re-sorting of the measurement data, it is advisable to interpolate measurement data between the data actually measured at the detector in order thus to generate a pseudo X-ray beam having the required geometry. In a geometry arranged in this way, the top and bottom boundary of the TD window TD can be described as follows in accordance with equation (7):

$$w_{top} = \frac{Dh}{R_0}\frac{\pi/2 - \arcsin(s_r/R_0)}{\sqrt{1 - s_r^2/R_0^2}}, \quad (10)$$

$$w_{bottom} = -\frac{Dh}{R_O}\frac{\pi/2 - \arcsin(s_r/R_0)}{\sqrt{1 - s_r^2/R_0^2}}$$

It will now be explained how differential back-projection on M-lines is performed. As already mentioned in the introduction, an M-line is a line connecting an X-ray source position to any point on the detector. To explain the concept of differential back-projection (DBP) on M-lines, the term DBP$\{\lambda_a, \lambda_b, \underline{x}\}$ will be used in the following to denote differential back-projection of the measurement values $g(\lambda, g, w)$ over the interval $[\lambda_a, \lambda_b]$ at the voxel position x. As the above-described rebinning step prior to performing back-projection gives a significant improvement in respect of efficiency and noise behavior, said differential back-projection is preferably performed in the rebinned geometry defined in accordance with equation (8). Analogously to the above designations, differential back-projection of the rebinned measurement values $g_r(\theta, s_r, w)$ over the interval $[\theta_a, \theta_b]$ at the voxel x in this geometry is denoted by DBP$_r\{\theta_a, \theta_b, \underline{x}\}$. The back-projection equation is then:

$$DBP_r\{\vartheta_a, \vartheta_b, \underline{x}\} = \int_{\vartheta_a}^{\vartheta_b} g_d(\vartheta, s_r^*(\vartheta, x), w^*(\vartheta, x))d\vartheta, \quad (11)$$

where:

$$g_d(\vartheta, s_r, w) = \frac{D}{\sqrt{D^2 + w^2}}\frac{\partial}{\partial s_r}g_r(\vartheta, s_r, w), \quad (12)$$

$$s_r^*(\vartheta, \underline{x}) = x\cos(\vartheta + \vartheta_0) + y\sin(\vartheta + \vartheta_0) \quad (13)$$

and $$w^*(\vartheta, \underline{x}) = \frac{D(z - z_0 - h(\vartheta - \pi/2 + \arcsin(s_r^*/R_0)))}{y\cos(\vartheta + \vartheta_0) - x\sin(\vartheta + \vartheta_0) + \sqrt{R_0^2 - s_r^{*2}}} \quad (14)$$

The two variants of differential back-projection (with and without rebinning) are connected mathematically by the equation $$DBP\{\lambda_a, \lambda_b, \underline{x}\} = DBP_r\{\vartheta^*(\lambda_a, \underline{x}), \vartheta^*(\lambda_b, \underline{x}), \underline{x}\} \quad (15)$$

with $$\vartheta^*(\lambda, \underline{x}) = \lambda + \frac{\pi}{2} - \gamma^*(\lambda, \underline{x}) \quad (16)$$

(cf. equation (9)) and $$\gamma^*(\lambda, \underline{x}) = \arctan\left(\frac{y\cos(\lambda + \lambda_0) - x\sin(\lambda + \lambda_0)}{R_0 - x\cos(\lambda + \lambda_0) - y\sin(\lambda + \lambda_0)}\right) \quad (17)$$

Whichever variant of differential back-projection is used, i.e. whether or not rebinning is first carried out, the result of back-projection is not the rendering of the wanted subject (i.e. the intensity of the respective reconstructed voxels), but instead its Hilbert transform along a particular line, in the present case along the above-described M-line. After back-projection, as already explained, inverse Hilbert transformation must be performed. As it is to be assumed that the wanted function ƒ(x) is only defined on a limited area, namely within the field of view, finite inverse Hilbert transformation can be carried out without difficulty. The precise procedure for inverse Hilbert transformation is described in the article H. Schöndube, K. Stiersdorfer, F. Dennerlein, T. White and F. Noo: "Towards an efficient two-step hilbert algorithm for helical cone-beam CT." in Proc. 2007 Meeting on Fully 3D Image Reconstruction in Radiology and Nuclear Medicine (Lindau, Germany), F. Beckman and M. Kachelrieβ, Eds., 2007, pp. 120-123 already mentioned above, the entire contents of each of which are hereby incorporated herein by reference, in which differential back-projection is likewise explained, but in that case onto the π-lines already mentioned in the introduction. As the π-lines, as mentioned, constitute a sub-group of the M-lines, the method described there for back-projection onto π-lines and subsequent inverse Hilbert transformation can, in a similar, appropriately modified manner, also be used for back-projection of M-line surfaces, so that reference is made to this publication in respect of the mathematical details.

In the following, the Hilbert transform of a wanted intensity value f(x) of a voxel at the location x along the unit vector ω is denoted by (Hf)(x, ω) and the unit vector from the point a(λ) in the direction of x is denoted by ω(λ,x). Using this notation, back-projection onto M-lines can be described as follows:

$$(Hf)(\underline{x},\omega(\lambda_M,\underline{x}))=DBP\{\lambda_M,\lambda_2(\underline{x}),\underline{x}\}-DBP\{\lambda_1(\underline{x}),\lambda_M,\underline{x}\} \quad (18)$$

Figure 2:
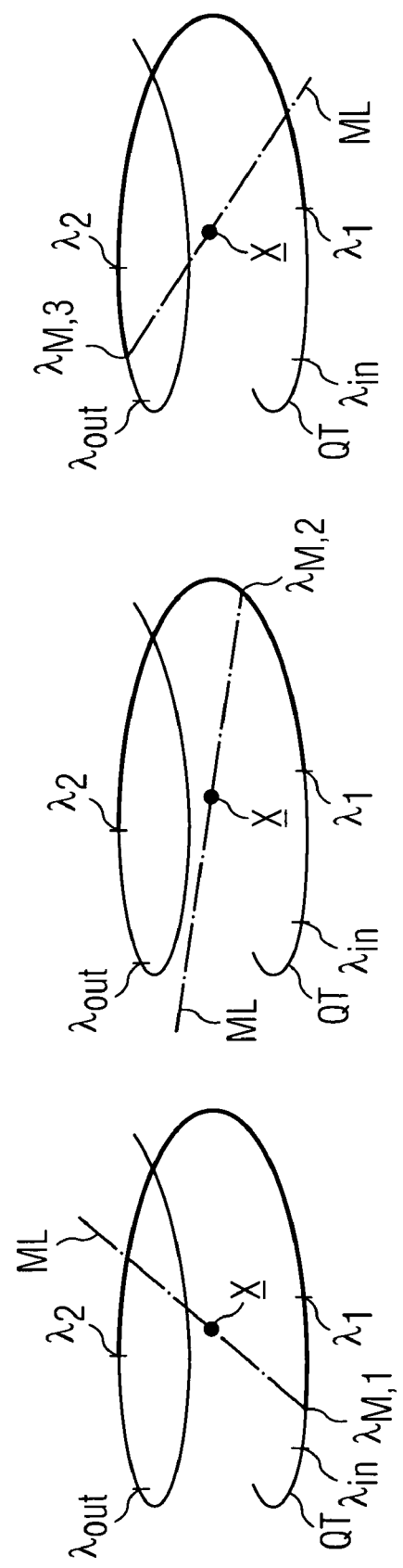
FIG. 2 schematically illustrates three different M-lines which intersect a particular voxel at the position $\bar{x}$, and the associated back-projection areas on the X-ray source trajectory.

This holds true for any voxel x inside the helix, as long as x has been irradiated for the complete back-projection interval. The source positions $a(\lambda_1(x))$ and $a(\lambda_2(x))$ correspond to the positions at which the projection of the voxel x is currently entering the TD window on the detector D or leaving it again. The line connecting the source position $a(\lambda_M)$ to x defines the direction of the Hilbert transform, i.e. the back-projection result changes with $\lambda_M$. Only after performing inverse Hilbert transformation is the reconstruction result mathematically independent of the selection of $\lambda_M$, it being unnecessary for $\lambda_M$ to lie in the interval between $\lambda_1(x)$ and $\lambda_2(x)$ by which the TD window is bounded. It is merely necessary that $\lambda_M$ lie such that the projection of the voxel x lies within the detector itself. The limits of this area are given by $\lambda_{in}(x)$ and $\lambda_{out}(x)$. The helix, i.e. the source trajectory QT and the coordinates λ, is shown in FIG. 2. The possibility of selecting $\lambda_M$ independently of the TD window shows that, in principle, redundant data measured outside the TD window TD can also be taken into account for the reconstruction.

FIG. 2 shows a representation of three different start points $\lambda_{M,1}$, $\lambda_{M,2}$, $\lambda_{M,3}$ for three different M-lines, the part of the source trajectory QT in bold print marking the source positions contributing to back-projection according to equation (18). In the case $(\lambda_M<\lambda_1(x))$ on the left, the entire back-projection interval extends from $\lambda_M$ to $\lambda_2(x)$. If $\lambda_M$ is between $\lambda_1(x)$ and $\lambda_2(x)$ (middle case with $\lambda_{M,2}$), the back-projection interval extends from $\lambda_1(x)$ to $\lambda_2(x)$. In the third case (right-hand side), $\lambda_M>\lambda_2(x)$ so that back-projection is performed over all λ from $\lambda_1(x)$ to $\lambda_{M,3}$. In the middle case, back-projection corresponds to using only data from the Tam-Danielsson interval. In the left-hand case, redundant data below the TD window and in the right-hand case above the TD window are also taken into account for back-projection. A more precise explanation of back-projection, but only for individual voxels, can be found in the already mentioned publication J. Pack, F. Noo and R. Clackdoyle: "Cone-beam reconstruction using the backprojection of locally filtered projections." IEEE Trans. Med. Imag., vol. 24, no. 1, pp. 70-85, January 2005, the entire contents of which is hereby incorporated herein by reference.

However, as already explained in the introduction, such back-projection for individual voxels is inefficient. Here, therefore, volume-based reconstruction is inventively performed over an entire family of parallel M-lines. For this purpose, the desired volume V to be completely reconstructed is subdivided into a stack of surfaces which are each constituted by a group of M-lines that are pairwise parallel to one another. Said pairwise parallel M-lines are selected such that they intersect the x/y-plane at the same angle, that their projections onto said x/y-plane are equidistant and parallel, and that they all point to the same detector row.

Figure 3:
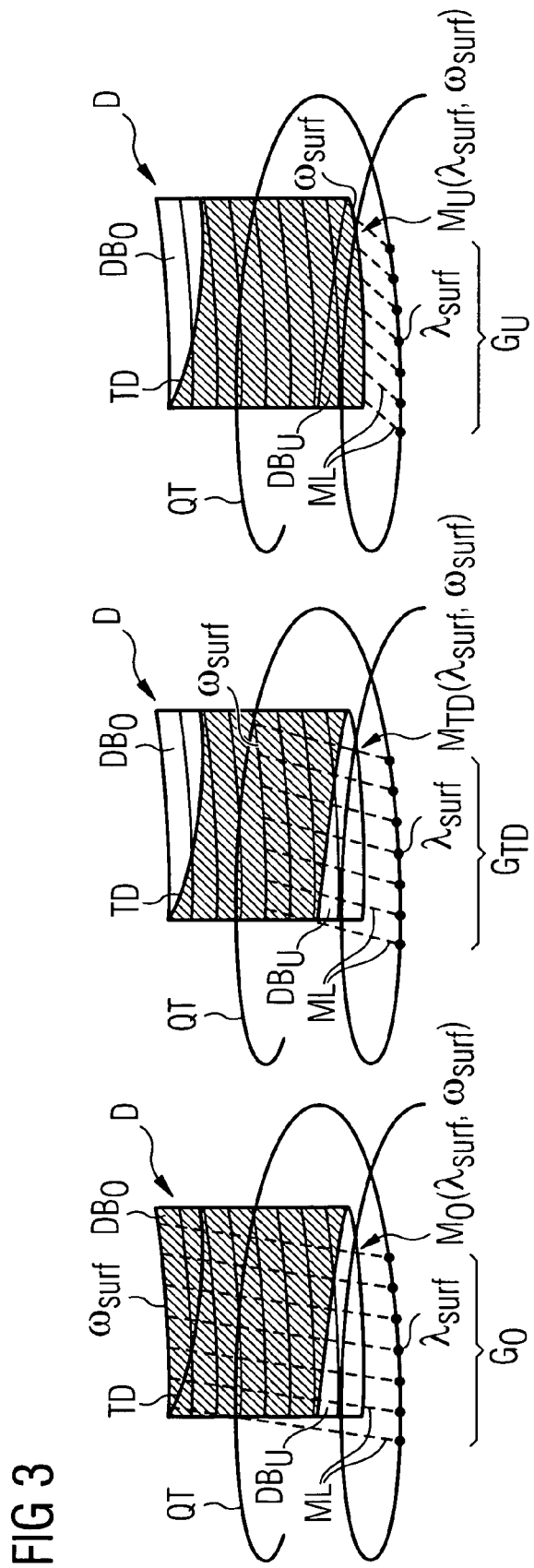
FIG. 3 shows three different types of M-line surfaces for use in an embodiment of the inventive reconstruction method, each represented schematically in respect of the X-ray source trajectory, a detector surface and the TD window on the detector surface.

This is depicted in FIG. 3 which—analogously to FIG. 2—again illustrates three variants, showing in each case the source trajectory QT, a schematic representation of the detector surface D and the Tam-Danielsson window TD formed thereon by the projection of the source trajectory QT. The source trajectory QT is here selected such that the TD window TD just fits into the surface of the detector D.

Here, each of the M-line surfaces $M_O(\lambda_{surf}, w_{surf})$, $M_{TD}(\lambda_{surf}, w_{surf})$, $M_U(\lambda_{surf}, w_{surf})$ is defined by a detector row $w_{surf}$ at which the relevant surface $M_O(\lambda_{surf}, w_{surf})$, $M_{TD}(\lambda_{surf}, w_{surf})$, $M_U(\lambda_{surf}, w_{surf})$ intersects the detector D, and by the direction of the M-lines ML which is given by the position $\lambda_{surf}$ on the source trajectory QT which is defined by the start point $a(\lambda_{surf})$ of the central M-line of the surface $M_O(\lambda_{surf}, w_{surf})$, $M_{TD}(\lambda_{surf}, w_{surf})$, $M_U(\lambda_{surf}, w_{surf})$ (i.e. the M-line which intersects the z-axis). In the context of this invention, the M-lines ML, which here each constitute a surface $M_O(\lambda_{surf}, w_{surf})$, $M_{TD}(\lambda_{surf}, w_{surf})$, $M_U(\lambda_{surf}, w_{surf})$, are each designated as a particular group $G_O$, $G_{TD}$, $G_U$ of M-lines ML.

In the middle of FIG. 3 a case is shown in which the surface $M_{TD}(\lambda_{surf}, w_{surf})$ formed by the M-lines ML intersects the detector D at a detector row which lies fully in the TD window TD. On the left-hand side a case is shown in which the surface $M_O(\lambda_{surf}, w_{surf})$ is above the TD window TD, namely exactly on the top edge of the detector D, i.e. on the topmost detector row. On the right-hand side the reverse case is shown in which the M-lines are selected such that the surface $M_U(\lambda_{surf}, w_{surf})$ formed thereby falls onto the bottom edge of the detector D, i.e. the lowest detector row and therefore lies below the TD window TD, the hatching in each case indicating the detector area from which measurement data is taken into account for volume-based back-projection on a surface $M_O(\lambda_{surf}, w_{surf})$, $M_{TD}(\lambda_{surf}, w_{surf})$, $M_U(\lambda_{surf}, w_{surf})$ formed by the respective M-lines. This clearly shows that, in the left-hand case, redundant data from an area $DB_O$ above the TD window TD is used, in the middle case only data inside the TD window TD is used, and in the right-hand case redundant data from a detector area $DB_U$ below the TD window TD is used.

In an example embodiment of the method according to the invention, the three surfaces are selected as shown schematically in FIG. 3, i.e. back-projections of the volume V are performed over three different stacks of surfaces, a surface stack being selected such that the surfaces $M_U(\lambda surf, w_{surf})$ each directly meet the lower edge of the detector D. For the second back-projection, i.e. reconstruction, a surface stack is selected such that the surfaces $M_{TD}(\lambda_{surf}, w_{surf})$ lie exactly in the TD window TD, and for the third back-projection a surface stack $M_O(\lambda surf, w_{surf})$ is selected such that the surfaces lie above the TD window TD on the upper edge of the detector D. This ensures that as much redundant data as possible is used and the detector D is fully utilized.

For the back-projection, the individual voxels on the surfaces defined by the M-lines are defined using an orthonormal grid (s, τ) which rotates with the direction of the M-lines along the source trajectory QT. These unity vectors of the co-rotating grid are defined by $$\underline{e}_s(\lambda_{surf})=[-\sin(\lambda_{surf}+\lambda_0),\cos(\lambda_{surf}+\lambda_0),0] \quad (19)$$

$$\underline{e}_\tau(\lambda_{surf})=[-\cos(\lambda_{surf}+\lambda_0),-\sin(\lambda_{surf}+\lambda_0),0] \quad (20)$$

In other words, the projections of the M-lines onto the x/y-plane are lines parallel to the unit vector $e_\tau$. These lines are at a signed distance s from the origin, s being measured positively in the direction of $e_s$ and τ being a coordinate along these lines. The Cartesian position of a point (s, τ) on a surface $M(\lambda_{surf}, w_{surf})$ constituted by M-lines is then given by $$x = -s\sin(\lambda_{surf} + \lambda_0) - \tau\cos(\lambda_{surf} + \lambda_0) \quad (21)$$

$$y = -s\cos(\lambda_{surf} + \lambda_0) - \tau\sin(\lambda_{surf} + \lambda_0) \quad (22)$$

$$z = z_0 + h\left(\lambda_{surf} + \arcsin\left(\frac{s}{R_0}\right)\right) + \frac{\tau + \sqrt{R_0^2 - s^2}}{D_R} \cdot w_{surf} \quad (23)$$

For a basic reconstruction of the desired volume $V(\underline{x})$ on a Cartesian grid of voxels of size ($\Delta x$, $\Delta y$, $\Delta z$), a constant value for $w_{surf}$ is now initially assumed and then a range of surfaces required to completely cover the volume V is calculated by varying $\lambda_{surf}$. We then set $$\Delta\lambda_{surf} = \Delta z/h, \quad (24)$$

and the differential back-projection and subsequent inverse Hilbert transformation are performed on these surfaces.

This is followed by conversion to Cartesian coordinates using an interpolation. The interpolation is performed in two steps. First an interpolation from the (s, $\tau$, $\lambda_{surf}$) grid to an intermediate coordinate system (x, y, $\lambda_{surf}$) is performed using equations (21) and (22), and finally conversion or rather interpolation into the Cartesian grid takes place using equation (23).

When these reconstructions of the same volume using three different groups of M-lines or rather surfaces have been performed (once with surfaces above the TD window, as shown in FIG. 3, left, once with surfaces in the middle of the TD window, as shown in FIG. 3, middle, and once with surfaces below the Tam-Danielsson window, as shown in FIG. 3, right), the thereby reconstructed volumes $V_1(\underline{x})$, $V_2(\underline{x})$, $V_3(\underline{x})$ are averaged according to $$V(\underline{x}) = \frac{V_1(\underline{x}) + V_2(\underline{x}) + V_3(\underline{x})}{3} \quad (25)$$

in order thus to produce the final reconstruction of the VoI. Equation (25) must be understood as meaning that, for example, the intensity is averaged for each individual voxel at the location x from the three reconstructions, i.e. an average intensity value is taken therefrom. In this way the required reconstructed volume $V(\underline{x})$ is formed. Obviously averaging of this kind can also be performed on a weighted basis. For example, the reconstruction from data originating only from the TD window can be given greater weight than the reconstructions which also contain redundant data.

Figure 4:
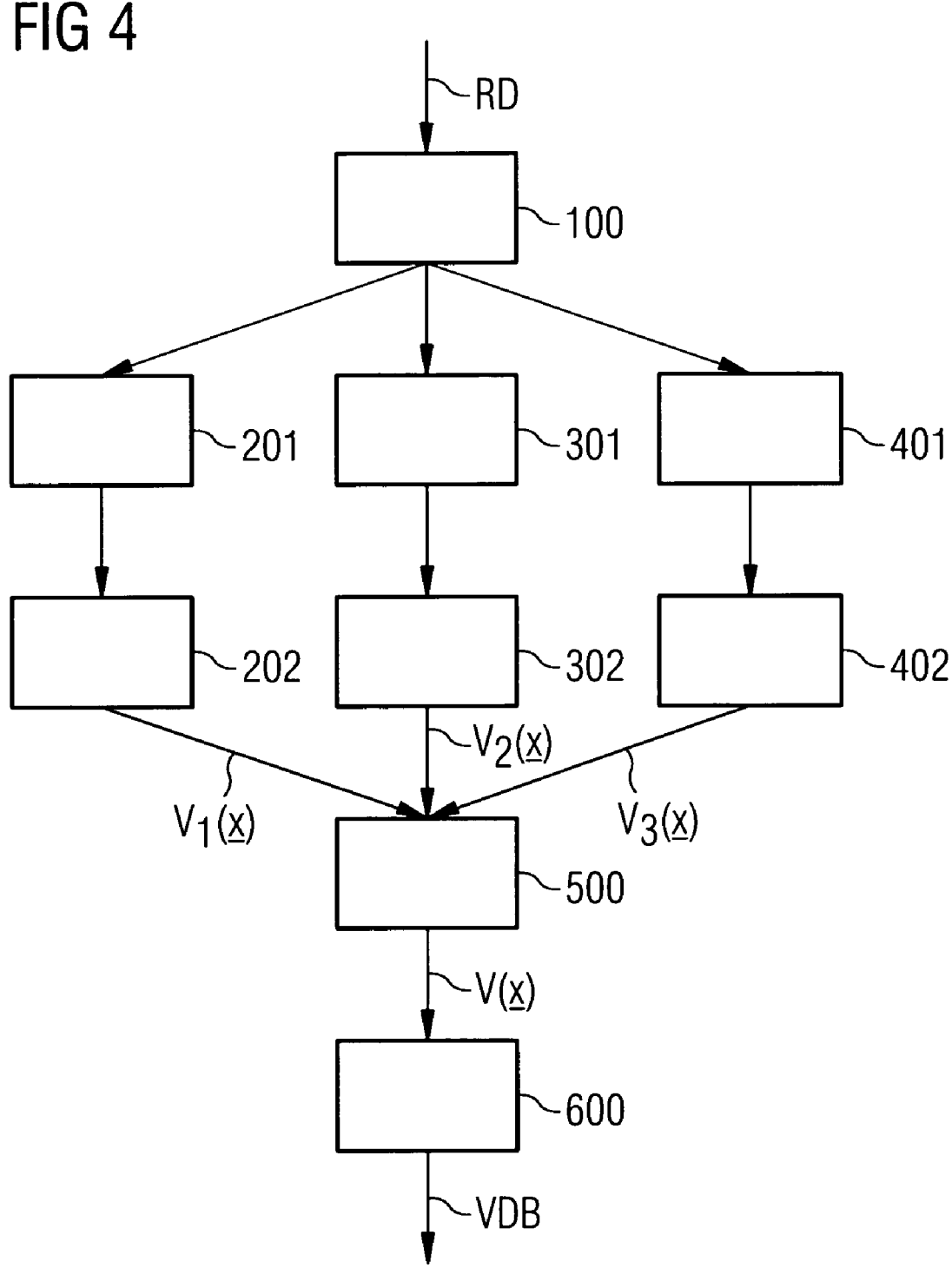
FIG. 4 shows a flowchart representing a possible method sequence of an embodiment.

FIG. 4 shows once again a preferred sequence of the method according to the invention on the basis of a flowchart.

In step 100 the acquired X-ray CT data sets, i.e. the raw data RD, are acquired and suitably pre-processed, e.g. cleaned up as far as possible.

In steps 201, 301 and 401, particular M-lines are then selected such that they form the desired surfaces below the TD window, in the TD window or above the TD window, and differential back-projection is then performed over them, as described above. Then, in steps 202, 302 and 402 inverse Hilbert transformation is performed in each case in order to produce the desired reconstructions. In a step 500, the volumes $V_1(\underline{x})$, $V_2(\underline{x})$, $V_3(\underline{x})$ reconstructed in the process are then suitably combined to form a desired volume $V(\underline{x})$. For example, averaging is performed as described above. In a step 600, the data thus produced is finally stored in a memory, output to a user as CT image data VBD or further processed in some other way, e.g. in order to generate slices therefrom and display them individually.

The step sequences 201 and 202, 301 and 302 and/or 401 and 402 can be carried out in parallel, as shown here. However, it is basically also possible to perform the reconstructions one after the other. This depends of the available computing capacity.

Figure 5:
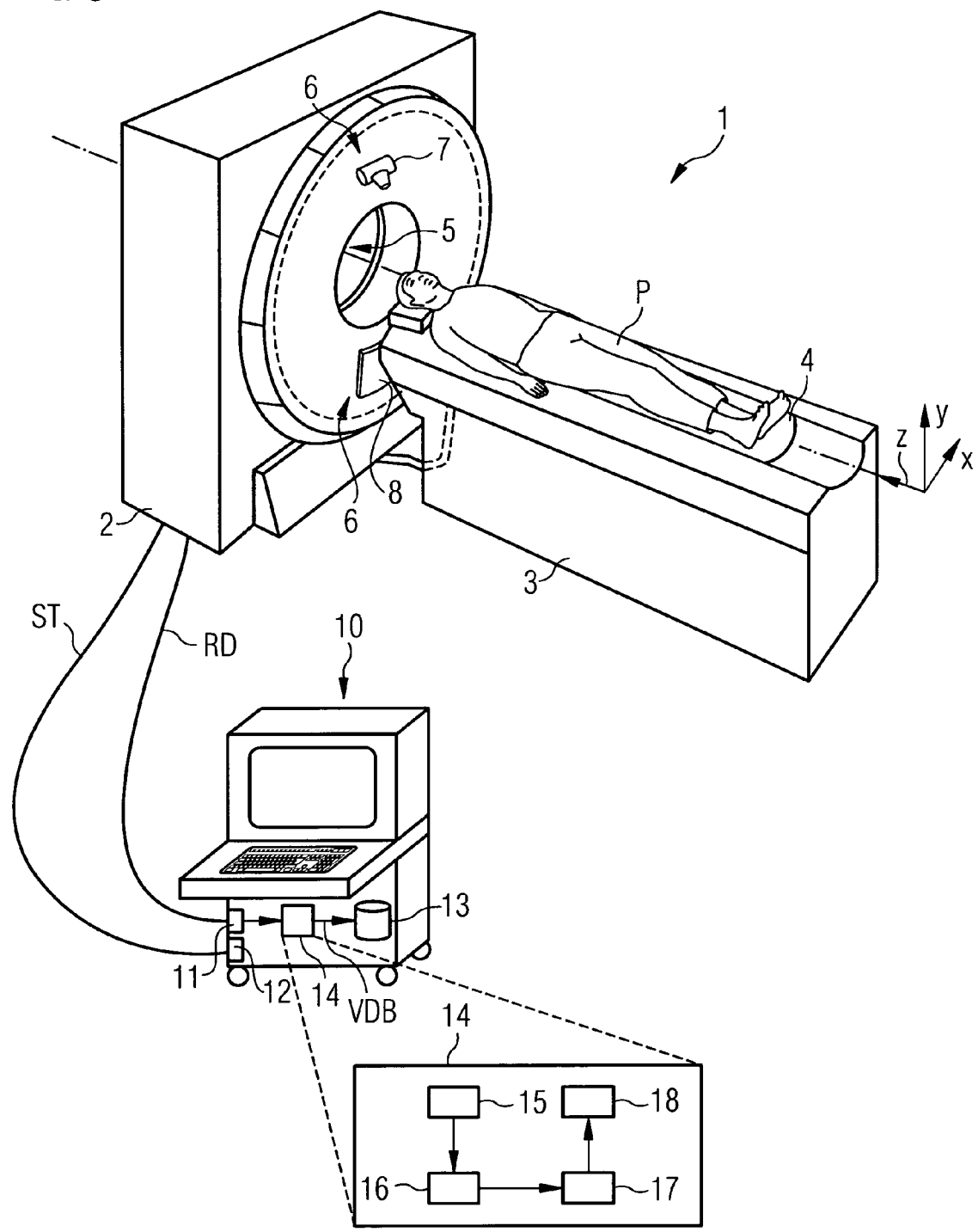
FIG. 5 is a highly schematic representation of a computed tomography system with an image reconstruction device according to an embodiment of the invention.

FIG. 5 schematically illustrates a computed tomography system 1 with an image reconstruction device 14 according to the invention, said CT system 1 essentially comprising a normal scanner 2 in which a detector system 6 with a detector 8 and an X-ray source 7 disposed opposite the detector 8 rotates around a scanning chamber 5 on a gantry. In front of the scanner 2 is a patient support device 3, i.e. a patient positioning table 3, whose upper section 4 with a patient P can be displaced relative to the scanner 2 in order to move the patient P through the scanning chamber 5 relative to the detector system 6. The scanner 2 and patient positioning table 3 are controlled by a control device 10 from which control data ST comes via a usual interface 12 in order to control the system in accordance with predefined scanning protocols in the conventional manner. The movement of the patient P along the z-direction, which corresponds to the system axis longitudinally through the scanning chamber 5, and the simultaneous rotation of the X-ray source 7 produce the above-explained helical path for the X-ray source 7 relative to the patient P during the scan, i.e. in relation to the coordinate system x, y, z fixedly defined on the patient, the X-ray source 7 describes the helical source trajectory QT during the scan, the detector 8 always running parallel to the X-ray source 7. Basically, however, the method can also be used on other CT systems, e.g. with a detector forming a complete ring. It is only essential that a helical scan is performed.

The raw data RD acquired by the detector 8 is transferred to a measurement data interface 11 of the control device 10. Said raw data RD is then further processed in an image reconstruction device 14 implemented in the control device 10 in the form of software on a processor.

The image reconstruction device 14 has, as shown enlarged, a raw data interface 15 for transferring the X-ray CT data sets RD. Said data RD is then forwarded to an X-ray CT data selection and calculation module 16 which, as described above, forms the M-line surfaces and performs the reconstructions thereover. The combination of the thereby generated reconstructed volume data or more specifically the above-described averaging takes place in a downstream volume image data combining module 17. The finished computed tomography volume image data is then transferred to an image data interface 18 which then, for example, stores the volume image data generated in a memory 13 of the control device 10 or outputs it in the usual manner to the screen 10 of the control device or injects the data via an interface (not shown) into a network connected to the computed tomography system, e.g. a radiological information system (RIS) or stores it in mass storage available there or outputs corresponding images to printers connected there. The data can also be further processed as required and then stored or output.

As already explained above, the method according to the invention provides a reconstruction technique that is mathematically exact and therefore, even in the case of very large detectors, prevents artifacts that could be caused by the conicity of the X-ray beam. By using the redundant data, a considerable reduction in image noise is nevertheless achieved and the introduced dose therefore fully utilized.

Finally, it should once again be pointed out that the above-described methods and devices are merely preferred examples of the invention and that the invention can be varied by the average person skilled in the art without departing from the scope of the invention in so far as it is specified by the claims. For the sake of completeness it should also be noted that the use of the indefinite article "a" or "an" does not rule out the possibility of the relevant features also being multiply present. Likewise the term "unit" or "module" does not preclude the latter consisting of a plurality of components which may possibly also be spatially distributed.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating computed tomography image data of a volume of interest from X-ray CT data sets generated by a computed tomography system during scanning of an examination subject on a helical path rotating around a longitudinal system axis in an infeed direction, the method comprising:

performing at least two volume-based reconstructions of the volume of interest by way of differential back-projection over surfaces constituted by different groups of M-lines, followed in each case by an inverse Hilbert transformation, the groups of M-lines for the reconstructions being selected from different of the following M-line subsets:

i) a first M-line subset, selected such that a surface constituted by the respective M-lines meets the detector surface completely within a Tam-Danielsson window, ii) a second M-line subset, selected such that a surface constituted by the respective M-lines intersects a detector area before the Tam-Danielsson window in the infeed direction, iii) a third M-line subset, selected such that a surface constituted by the respective M-lines intersects a detector area after the Tam-Danielsson window in the infeed direction; and combining different reconstructed volumes to form a final reconstruction of the volume of interest.

2. The method as claimed in claim 1, wherein for combining the different reconstructed volumes, the reconstructed volumes are averaged.

3. The method as claimed in claim 2, wherein at least one of the different reconstructions is carried out using a group of M-lines from the first M-line subset, and at least one other of the reconstructions is carried out using a group of M-lines from the second or third M-line subset.

4. The method as claimed in claim 3, wherein at least one reconstruction is performed using a group of M-lines from the first M-line subset, at least one reconstruction is performed using a group of M-lines from the second M-line subset, and at least one reconstruction is performed using a group of M-lines from the third M-line subset.

5. The method as claimed in claim 1, wherein at least one of the different reconstructions is carried out using a group of M-lines from the first M-line subset, and at least one other of the reconstructions is carried out using a group of M-lines from the second or third M-line subset.

6. The method as claimed in claim 5, wherein at least one reconstruction is performed using a group of M-lines from the first M-line subset, at least one reconstruction is performed using a group of M-lines from the second M-line subset, and at least one reconstruction is performed using a group of M-lines from the third M-line subset.

7. The method as claimed in claim 1, wherein the volumes reconstructed during the individual reconstructions are first transformed into Cartesian coordinates and the reconstructed volumes are combined within said coordinate system.

8. The method as claimed in claim 1, wherein interpolated detector data is used to perform the reconstructions.

9. The method as claimed in claim 8, wherein the detector data is interpolated between actually measured detector data such that the M-lines constituting the respective surface appear projected in parallel onto a plane perpendicular to the longitudinal system axis of a computed tomography system used for acquiring the X-ray CT data sets.

10. The method as claimed in claim 8, wherein the interpolated detector data for implementing the M-lines constituting the respective surface are selected such that the M-lines in question are implemented in an equidistant manner.

11. The method as claimed in claim 1, wherein the M-lines constituting the respective surface are selected such that they fall on the same detector row.

12. The method as claimed in claim 1, wherein an X-ray source trajectory rotating in a helical manner around the region of interest is selected such that a Tam-Danielsson window defined by the X-ray source trajectory on the detector surface is adjacent to the outer edges of the two outermost detector rows.

13. A computer-readable medium encoded with a computer program product which can be loaded directly into a memory of a programmable image reconstruction device, including program code sections for performing the method of claim 1 when the program is executed in the image reconstruction device.

14. A programmable image reconstruction device including a memory, the memory including program code sections for performing the method of claim 1 when the program code sections are executed in the programmable image reconstruction device.

15. A computer readable medium including program segments for, when executed on a computer device, causing the computer device to implement the method of claim 1.

16. An image reconstruction device for generating computed tomography image data of a volume of interest from X-ray CT data sets generated during scanning of the examination subject on a helical path rotating about a longitudinal system axis in an infeed direction, comprising:
  a raw data interface for transferring X-ray CT data sets;
  an X-ray CT data selection and calculation module, designed to perform at least two volume-based reconstructions of the volume of interest by way of differential back-projection over surfaces constituted by groups of M-lines, followed in each case by an inverse Hilbert transformation and, in doing so, to select the groups of M-lines for the reconstructions from different of the following M-line subsets:
  i) a first M-line subset, selected such that a surface constituted by the respective M-lines meets the detector surface completely within a Tam-Danielsson window,
  ii) a second M-line subset, selected such that a surface constituted by the respective M-lines intersects a detector area before the Tam-Danielsson window in the infeed direction,
  iii) a third M-line subset, selected such that a surface constituted by the M-lines intersects a detector area after the Tam-Danielsson window in the infeed direction;
  a volume image data combining unit for combining the different reconstructed volumes to form a final reconstruction of the volume of interest; and
  an image data interface for outputting the computed tomography image data generated.

17. A computed tomography system including an image reconstruction device as claimed in claim 16.

* * * * *